United States Patent
Feloney

(10) Patent No.: US 9,108,020 B1
(45) Date of Patent: Aug. 18, 2015

(54) FEMALE URETHRAL CATHETERIZATION DEVICE

(76) Inventor: Michael Feloney, Omaha, NE (US)

(*) Notice: Subject to any disclaimer, the term of this patent is extended or adjusted under 35 U.S.C. 154(b) by 1 day.

(21) Appl. No.: 12/875,577

(22) Filed: Sep. 3, 2010

(51) Int. Cl.
- A61M 27/00 (2006.01)
- A61M 25/00 (2006.01)
- A61M 25/01 (2006.01)
- A61B 17/34 (2006.01)

(52) U.S. Cl.
CPC .......... *A61M 27/008* (2013.01); *A61M 25/007* (2013.01); *A61M 25/0017* (2013.01); *A61M 25/0041* (2013.01); *A61M 25/0043* (2013.01); *A61M 25/0068* (2013.01); *A61B 17/3415* (2013.01); *A61B 17/3417* (2013.01); *A61M 25/00* (2013.01); *A61M 25/002* (2013.01); *A61M 2025/0191* (2013.01); *A61M 2202/0496* (2013.01); *A61M 2210/1085* (2013.01); *A61M 2210/1089* (2013.01)

(58) Field of Classification Search
CPC .......... A61M 25/0017; A61M 25/002; A61M 25/0054; A61M 25/0069; A61M 25/007; A61M 25/008; A61M 27/008; A61M 25/0111; A61M 25/0068; A61M 2210/1085; A61M 2210/1089; A61M 25/0043; A61M 2025/0191; A61M 2202/0496; A61M 25/00; A61M 25/0041; A61B 17/3415; A61B 17/3417; A61B 17/06109; A61B 2017/0608
USPC ............ 604/544, 27, 48, 73, 93.01, 264, 540, 604/541, 543, 326; 600/29, 573, 574, 580, 600/581, 582, 585
See application file for complete search history.

(56) References Cited

U.S. PATENT DOCUMENTS

| | | | | |
|---|---|---|---|---|
| 3,867,945 A * | 2/1975 | Long | | 604/170.02 |
| 3,908,637 A * | 9/1975 | Doroshow | | 600/573 |
| 3,920,023 A * | 11/1975 | Dye et al. | | 604/506 |
| 4,790,810 A * | 12/1988 | Pugh | | 604/8 |
| 4,986,823 A | 1/1991 | Anderson et al. | | |
| 4,995,872 A | 2/1991 | Ferrara | | |
| 5,045,078 A | 9/1991 | Asta | | |
| 5,116,309 A * | 5/1992 | Coll | | 604/8 |
| 5,152,749 A * | 10/1992 | Giesy et al. | | 604/164.01 |
| 5,334,185 A * | 8/1994 | Giesy et al. | | 604/170.01 |
| 5,356,382 A * | 10/1994 | Picha et al. | | 604/105 |
| 5,454,798 A * | 10/1995 | Kubalak et al. | | 604/328 |
| 5,472,435 A * | 12/1995 | Sutton | | 604/540 |
| 5,582,611 A | 12/1996 | Tsuruta et al. | | |
| 5,653,700 A | 8/1997 | Byrne et al. | | |
| 5,681,274 A * | 10/1997 | Perkins et al. | | 604/8 |
| 5,730,150 A | 3/1998 | Peppel et al. | | |
| 5,772,670 A | 6/1998 | Brosa | | |
| 6,063,063 A * | 5/2000 | Harboe et al. | | 604/256 |
| 6,379,334 B1 * | 4/2002 | Frassica | | 604/165.04 |
| 6,695,831 B1 * | 2/2004 | Tsukada et al. | | 604/544 |
| 2002/0002363 A1 * | 1/2002 | Urakawa et al. | | 604/544 |
| 2002/0130059 A1 | 9/2002 | Armijo | | |
| 2003/0004496 A1 * | 1/2003 | Tanghoj | | 604/544 |

(Continued)

*Primary Examiner* — Adam Marcetich
(74) *Attorney, Agent, or Firm* — Suiter Swantz pc llo

(57) ABSTRACT

The female urethral catheterization device may include an insertion portion configured for insertion into a urethra. The insertion portion having an opening for receiving a bodily fluid. The catheterization device may include an elongated portion configured for receiving a guiding input. The guiding input may be relayed from the elongated member to the insertion portion for guiding the insertion portion. The catheterization device may include a curved portion connecting the elongated portion and the insertion portion. The curved portion may have a drain for draining the bodily fluid.

12 Claims, 5 Drawing Sheets

(56) References Cited

U.S. PATENT DOCUMENTS

| | | | |
|---|---|---|---|
| 2003/0135200 A1* | 7/2003 | Byrne | 604/544 |
| 2005/0070882 A1* | 3/2005 | McBride | 604/544 |
| 2005/0192560 A1* | 9/2005 | Walls et al. | 604/544 |
| 2005/0246038 A1* | 11/2005 | O'Keefe et al. | 623/23.64 |
| 2006/0025753 A1* | 2/2006 | Kubalak et al. | 604/544 |
| 2006/0047268 A1 | 3/2006 | Stephens | |
| 2006/0206213 A1* | 9/2006 | Hammond et al. | 623/23.66 |
| 2007/0016169 A1* | 1/2007 | Utas et al. | 604/544 |
| 2008/0139877 A1* | 6/2008 | Chu et al. | 600/30 |
| 2008/0275463 A1* | 11/2008 | High | 606/108 |
| 2009/0088786 A1 | 4/2009 | Zook et al. | |
| 2010/0056910 A1 | 3/2010 | Yanuma | |
| 2010/0213238 A1 | 8/2010 | Farascioni et al. | |
| 2010/0241105 A1* | 9/2010 | Meade et al. | 606/1 |
| 2010/0256580 A1 | 10/2010 | Faber | |
| 2010/0324540 A1* | 12/2010 | Paulen et al. | 604/544 |
| 2011/0313361 A1 | 12/2011 | Shipman | |
| 2012/0248170 A1 | 10/2012 | Marczyk | |

* cited by examiner

FEMALE URETHRAL CATHETERIZATION DEVICE

TECHNICAL FIELD

The present disclosure relates generally to the field of personal medical devices, and more particularly to a device for urethral catheterization.

BACKGROUND

A person may need assistance with the excretion of bodily fluid. More particularly a female may need assistance with the excretion of bodily fluid. Assistance may be needed each time the bladder fills necessitating regular catheterization. However, female catheterization can be particularly troublesome because the urethra meatus may be difficult to access.

SUMMARY

The present disclosure is directed to a device that may allow a patient easier access to the urethra, especially if the patient is disabled, and may allow for an unobstructed flow of urine into a urine collector without contaminating the hands with bodily fluids or urine.

The female urethral catheterization device may include an insertion portion configured for insertion into a urethra. The insertion portion having an opening for receiving a bodily fluid. The catheterization device may include an elongated portion configured for receiving a guiding input. The guiding input may be relayed from the elongated member to the insertion portion for guiding the insertion portion. The catheterization device may include a curved portion configured for connecting the elongated portion and the insertion portion. The curved portion may have a drain for draining the bodily fluid.

The female urethral catheterization device may include an insertion portion configured for insertion into a urethra. The insertion portion having an opening for receiving a bodily fluid. The catheterization device may include an elongated portion configured for receiving a guiding input. The guiding input may be relayed from the elongated member to the insertion portion for guiding the insertion portion. The catheterization device may include a curved portion connecting the elongated portion and the insertion portion. The curved portion having a drain for draining the bodily fluid. The catheterization device may further include a handle coupled to the elongated portion. The handle being configured for receiving the guiding input from a hand.

The female urethral catheterization device may include a first portion having an insertion end and a curved end. The insertion end may be configured for insertion into a urethra and may have an opening for receiving bodily fluid. The curved end may have a drain for draining the bodily fluid. The catheterization device may include a second portion configured for receiving a guiding input from a hand. The guiding input may be relayed from the second portion to the first portion for guiding the insertion end. The catheterization device may also include a connector member for connecting the first portion to the second portion.

It is to be understood that the foregoing general description and the following detailed description are exemplary and explanatory only, and are not necessarily restrictive of the disclosure. The accompanying drawings, which are incorporated in and constitute a part of the specification, illustrate subject matter of the disclosure and together with the general description, serve to explain the principles of the invention. The disclosed invention will be understood by those skilled in the art from the following detailed description and drawings.

BRIEF DESCRIPTION OF THE DRAWINGS

The numerous advantages of the present invention may be better understood by those skilled in the art by reference to the accompanying figures in which.

DETAILED DESCRIPTION

Figure 1:
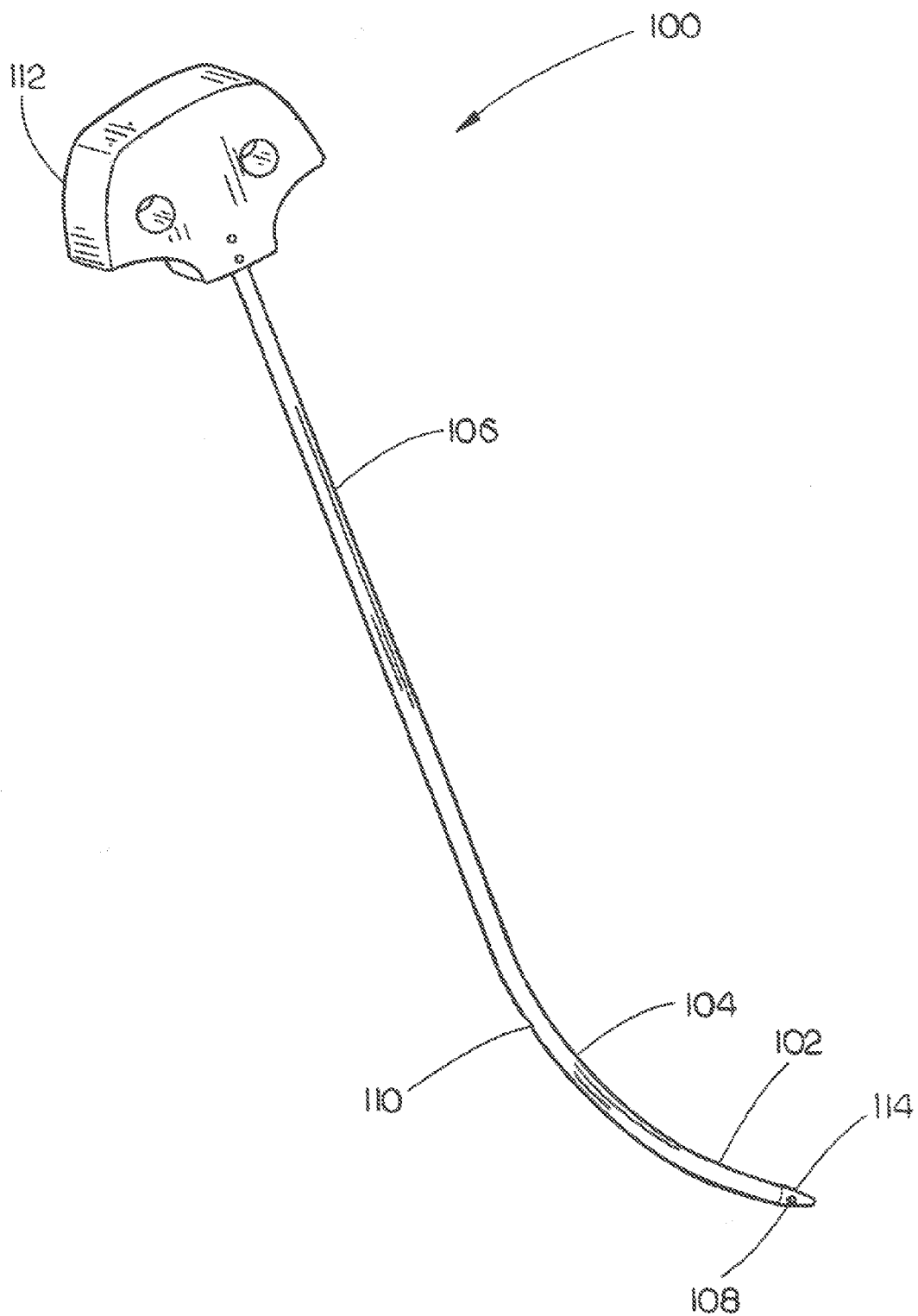
FIG. 1 depicts a catheterization device in accordance with an exemplary embodiment of the disclosure.

Reference will now be made in detail to the subject matter disclosed, which is illustrated in the accompanying figures.

Various situations may arise when it is necessary to assist with the excretion of bodily fluid from a bladder. In such situations a catheter may be inserted into the bladder via the urethra to assist the excretion of bodily fluid from the bladder. The present disclosure is directed to a urethral catheterization device which may be particularly suited for females.

Female catheterization may be particularly troublesome because the urethra meatus may be difficult to access. Furthermore, the catheter may be inserted into the vaginal opening by mistake due to the proximity of the urethra to the vaginal opening. If the catheter is inserted into the vagina and then taken out and inserted into the urethra, contaminants may be introduced into the urethra leading to infections. U.S. patent application Ser. No. 12/378,266 filed on Feb. 11, 2009 "Vaginal Barrier and Female Urethral Catheterization Assisting Device" discloses a device for assisting with the troublesome nature of female catheterization.

It is contemplated that the present disclosure may be used in conjunction with U.S. patent application Ser. No. 12/378, 266 "Vaginal Barrier and Female Urethral Catheterization Assisting Device" to allow a patient to self-catheterize herself using one hand.

Referring to FIGS. 1-4, diagrams illustrating embodiments of the female urethral catheterization device 100 are shown. The catheterization device 100 may have an insertion portion 102 configured for insertion into the bladder through the urethra, an elongated portion 106 configured for receiving a guiding input, and a curved portion 104 connecting the insertion portion 102 to the elongated portion 106. The guiding input may be provided by the user through a hand movement, wherein the guiding input is relayed to the insertion portion 102 for guiding the insertion portion 102. It is contemplated that the guiding input may be provided by any directing object including a robotic instrument, machine, or person. Insertion portion 102 may include one or more openings 108 for receiving the bodily fluid and curved portion 104 may include one or more drains 110 for draining the bodily fluid. Openings 108 and drains 110 are configured for assisting the excretion of bodily fluid from the bladder.

The insertion portion 102 is configured for inserting openings 108 through the urethra and into the bladder. Insertion portion 102 may include a tapered insertion tip 114 configured for facilitating insertion. One or more openings 108 may be located in the tapered insertion tip 114 or in proximity to the tapered insertion tip 114.

The curved portion 104 is configured for relaying the guiding input from the elongated portion 106 to the insertion portion 102. Curved portion 104 may be a single curvature or a plurality of curvatures and each curvature may be any angle or any combination of angles. Curved portion 104 may include one or more drains 110 for draining bodily fluid. Drains 110 may be located on the curved portion 104 for directing the draining of the bodily fluid. In one embodiment, the drains 110 may be located on the convex section of the curved portion 104.

The elongated portion 106 is configured for receiving a guiding input which is relayed to the insertion portion 102 for guiding the insertion portion 102. Elongated portion 106 may take on a variety of forms suitable for receiving the guiding input. Elongated portion 106 may be further configured for receiving a handle 112.

Figure 3:
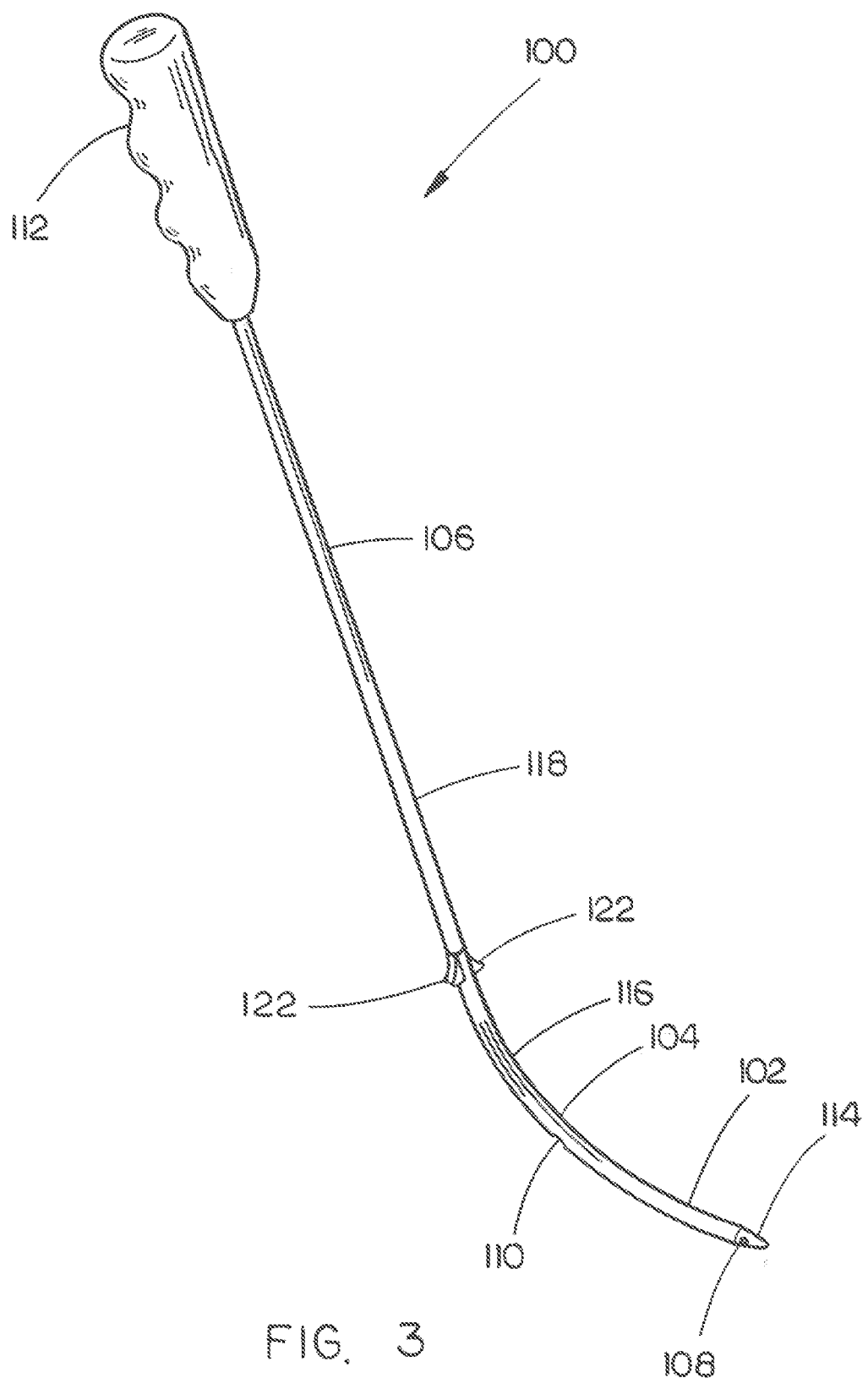
FIG. 3 depicts an alternative embodiment of the catheterization device.
Figure 5:
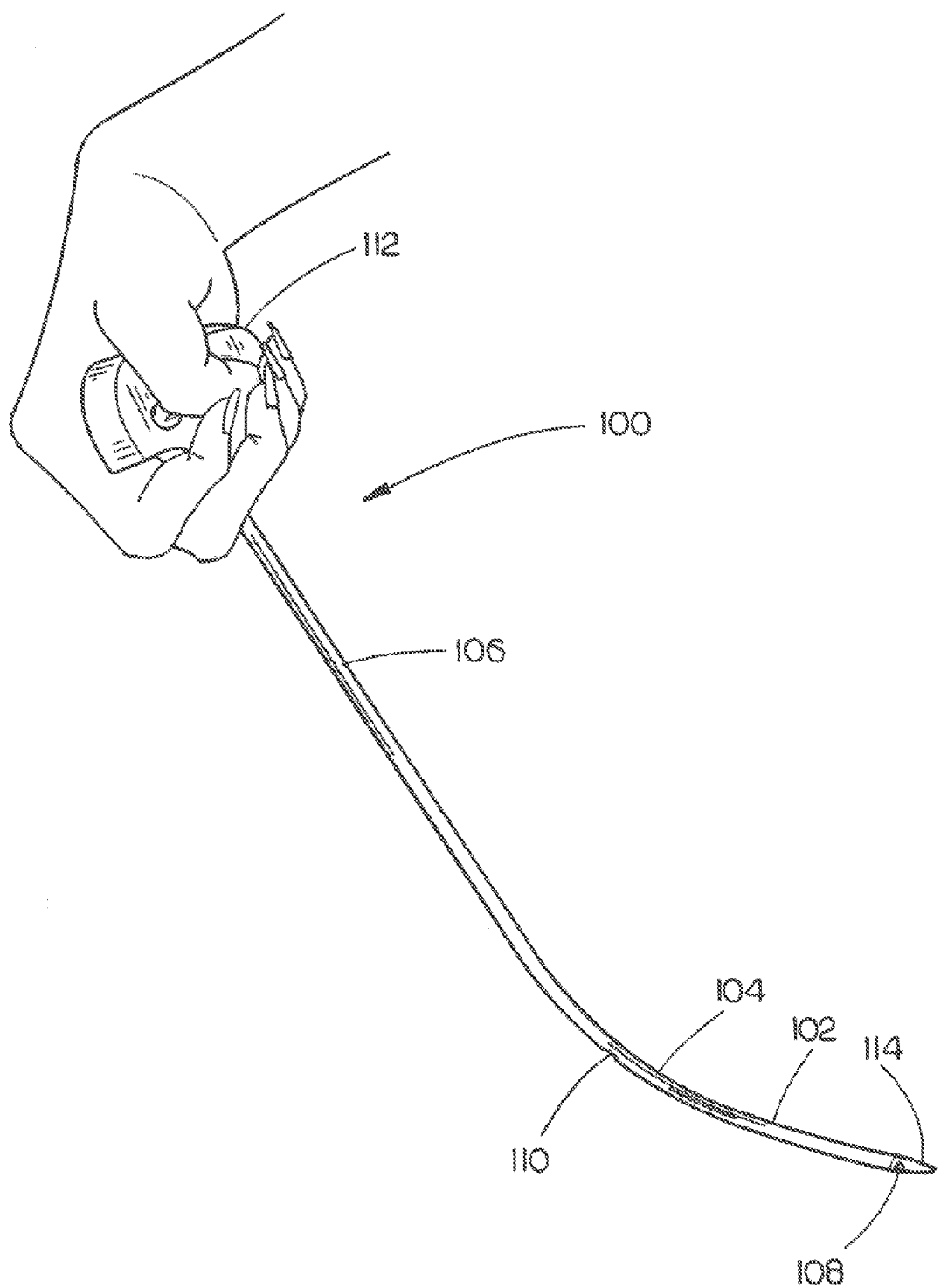
FIG. 5 depicts an exemplary embodiment of the present disclosure prepared for one handed self-catheterization.

Handle 112 may be configured for receiving a guiding input from a hand. The guiding input is relayed to the insertion portion 102 for guiding the insertion portion 102. Handle 112 may vary in structure, form and configuration. It is contemplated that the elongated portion 106 may form a handle 112 or that a handle 112 may be coupled to the elongated member 106. In one embodiment handle 112 is configured so that catheterization device 100 is substantially perpendicular to the handle grip as illustrated in FIG. 1 and FIG. 5. In another embodiment handle 112 is configured so that catheterization device 100 is substantially parallel to the handle grip as illustrated in FIG. 3.

Figure 2:
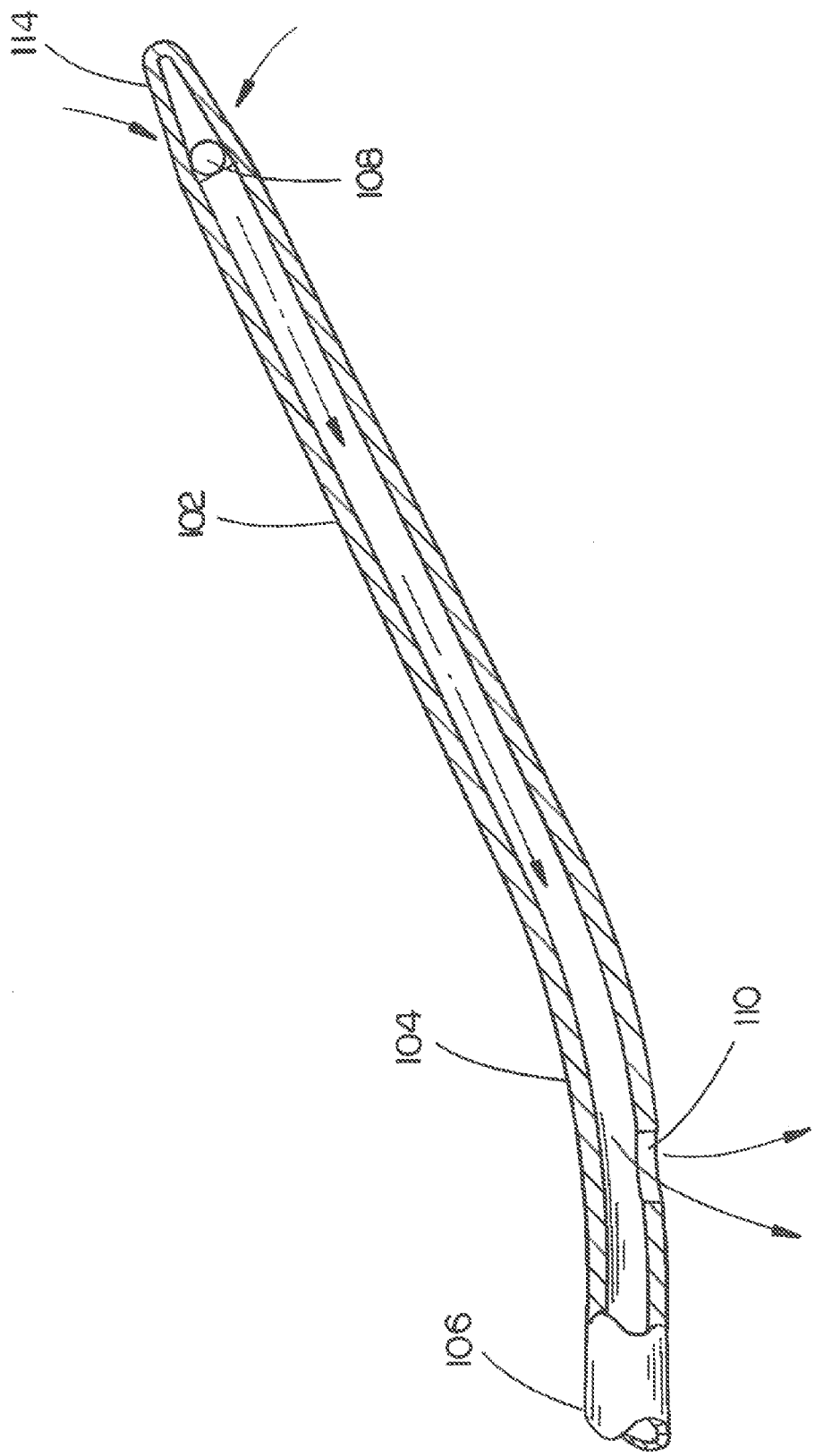
FIG. 2 depicts a partial cross-sectional view of the insertion portion and the curved portion.

Referring specifically to FIG. 2, a partial cross-sectional view of the insertion portion 102 and the curved portion 104 is shown. Insertion tube 102 may be inserted into the urethra so that the tapered tip 114 and one or more openings 108 may enter the bladder. Bodily fluid from the bladder may enter the insertion tube 102 through openings 108, and travel through the insertion tube 102 and the curved portion 104 to the one or more drains 110. Bodily fluid may exit the drains 110 allowing bodily fluid to be excreted from the bladder.

In one embodiment, catheterization device 100 may be configured as a single piece unit as illustrated in FIG. 1. For example, the catheterization device 100 may be constructed of a single material or a plurality of materials joined to form a single piece unit. A variety of materials may be used (including but not limited to vinyl, plastic, rubber, latex, Teflon, metal, silicone and the like) to provide the strength, rigidity, and comfort desirable for catheterization, guided by the guiding input received through the elongated portion 106.

In another example, catheterization device 100 may be configured as a multiple piece assembly. A piece of the multiple piece assembly may be constructed of a single material or a plurality of materials joined to form a single piece. It is contemplated that each piece may vary in structure, form and composition. It may be appreciated to be able to remove and replace the portion or portions of the multiple piece assembly which contact the urethra and bodily fluids and present a greater risk for infection.

Figure 4:
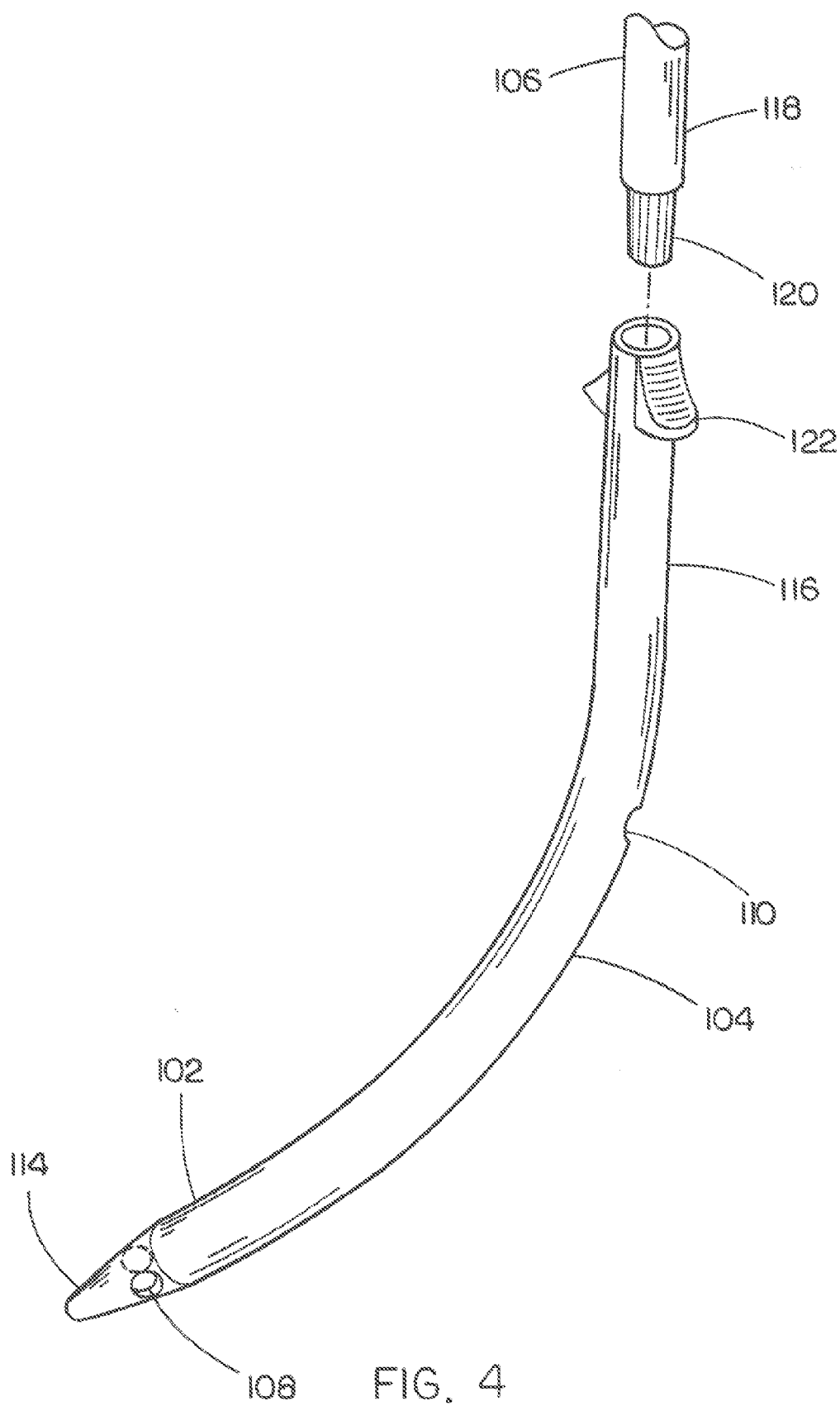
FIG. 4 depicts a partial view of a first piece and a second piece in accordance with an alternative embodiment of the disclosure.

Referring to FIG. 3 and FIG. 4, a specific embodiment of catheterization device 100 having a plurality of pieces is shown. Catheterization device 100 includes a first portion 116, a second portion 118, and a connector 120 (as illustrated in FIG. 4) configured for connecting the first portion 116 and the second portion 118. The first portion 116 may include an insertion end 102 and a curved end 104. Insertion end 102 may be configured for insertion into a urethra and may have an opening 108 for receiving bodily fluid. Curved end 104 may have a drain 110 for draining bodily fluid. The second portion 118 may be configured for receiving a guiding input from a hand. First portion 116 and second portion 118 may be connected together with connector 120, wherein the guiding input may be relayed from the second portion 118 to the first portion 116 for guiding the insertion end 102 for catheterization. In this configuration, the first portion 116 may be removed and replaced with a different (e.g. new or clean) first portion 116. It is contemplated that the first portion 116 may be disposable. It is further contemplated that the first portion 116 may be manufactured of a material that is water soluble, allowing first portion 116 to be flushed into a sewage system. First portion 116 may include a flange 122 configured for facilitating the coupling and decoupling of the first portion 116 and the second portion 118.

Connector 120 may include any member configured for coupling a first portion 116 and a second portion 118 (e.g., compression member, threaded member, latching member, hooking member, magnetic member, and the like). In one example, connector 120 may be a tubular structure configured to create a compression fit between the first portion 116 and the second portion 118. Connector 120 may further include striations or ridges to inhibit movement about the connector 120. Connector 120 may couple the first portion 116 and second portion 118 so that the first portion 116 and the second portion 118 may function as a single piece as illustrated in FIG. 3.

Referring specifically to FIG. 5, a hand providing guiding input is shown. Guiding input from the hand is received by the handle 112 which relays the guiding input through the elongated portion 106 and curved portion 104 to the insertion portion 102. Insertion portion 102 is guided by the guiding input into the urethra for catheterization. Catheterization device 100 may allow for one handed catheterization including one handed self-catheterization.

It is contemplated that the present invention may be used in conjunction with U.S. patent application Ser. No. 12/378,266 "Vaginal Barrier and Female Urethral Catheterization Assisting Device" to allow a patient to self-catheterize herself using one hand. However, users of the present invention may include a patient, urologist, physician support staff, and the like trained personnel.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A catheterization device, comprising:
a rigid curved portion connecting the rigid elongated portion and the rigid insertion portion, the rigid curved portion having only a single drain for allowing the bodily fluid to exit the catheterization device and drain into a fluid receptacle;
wherein the guiding input is relayed to the rigid insertion portion for guiding the rigid insertion portion, and the handle is configured to allow a patient to insert the rigid insertion portion into the patient's urethra and remove the catheterization device when drainage is complete.

2. The catheterization device of claim 1, wherein the insertion portion, elongated portion and rigid curved portion are configured as a single piece unit.

3. The catheterization device of claim 1, wherein the insertion portion, elongated portion and curved portion are configured as a multiple piece assembly, wherein the insertion portion and curved portion are configured as a single piece unit.

4. The catheterization device of claim 1, wherein the insertion portion includes a tapered insertion tip.

5. The catheterization device of claim 4, wherein the opening is in proximity to the tapered insertion tip.

6. The catheterization device of claim 1, wherein the drain is on a convex section of the rigid curved portion, the drain in proximity to the elongated portion.

7. A catheterization device, comprising:
   a rigid curved portion connecting the rigid elongated portion and the rigid insertion portion, the rigid curved portion having only a single drain for allowing the bodily fluid to exit the catheterization device and drain into a fluid receptacle;
   wherein the guiding input is relayed to the rigid insertion portion for guiding the rigid insertion portion and removing the catheterization device when drainage is complete, and wherein the rigid insertion portion and rigid curved portion comprise a substantially hollow tube.

8. The catheterization device of claim 7, wherein the insertion portion, elongated portion and rigid curved portion are configured as a single piece unit.

9. The catheterization device of claim 7, wherein the insertion portion, elongated portion and curved portion are configured as a multiple piece assembly, wherein the insertion portion and curved portion are configured as a single piece unit.

10. The catheterization device of claim 7, wherein the insertion portion includes a tapered insertion tip.

11. The catheterization device of claim 10, wherein the opening is in proximity to the tapered insertion tip.

12. The catheterization device of claim 7, wherein the drain is on a convex section of the rigid curved portion, the drain in proximity to the elongated portion.

\* \* \* \* \*